US006812188B2

United States Patent
Seo et al.

(10) Patent No.: US 6,812,188 B2
(45) Date of Patent: Nov. 2, 2004

(54) CATALYST FOR METHACRYLIC ACID PRODUCTION, COATED CATALYST, AND PROCESS FOR PRODUCING THE SAME

(75) Inventors: Yoshimasa Seo, Gunma (JP); Atsushi Sudo, Yamaguchi (JP); Hideki Sugi, Gunma (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/380,361

(22) PCT Filed: Sep. 13, 2001

(86) PCT No.: PCT/JP01/07955
§ 371 (c)(1),
(2), (4) Date: Mar. 13, 2003

(87) PCT Pub. No.: WO02/24328
PCT Pub. Date: Mar. 28, 2002

(65) Prior Publication Data
US 2004/0029724 A1 Feb. 12, 2004

(30) Foreign Application Priority Data

Sep. 21, 2000 (JP) ........................................ 2000-286326
Dec. 8, 2000 (JP) ........................................ 2000-373761

(51) Int. Cl.$^7$ .......................... B01J 27/14; B01J 27/198; B01J 27/188; B01J 27/19; B01J 27/185
(52) U.S. Cl. .................... 502/208; 502/209; 502/210; 502/211; 502/212; 502/213
(58) Field of Search ................................. 502/208–213

(56) References Cited

U.S. PATENT DOCUMENTS

| 4,301,031 | A |   | 11/1981 | Shaw et al. ................. 252/435 |
| 4,489,170 | A | * | 12/1984 | Krabetz et al. ............. 502/211 |
| 4,595,778 | A | * | 6/1986  | Duembgen et al. ......... 560/208 |
| 4,925,823 | A | * | 5/1990  | Krabetz et al. ............. 502/211 |
| 4,925,980 | A | * | 5/1990  | Matsumoto et al. ........ 562/534 |
| 5,104,844 | A |   | 4/1992  | Yamamoto et al. ......... 502/200 |
| 5,126,307 | A | * | 6/1992  | Yamamoto et al. ......... 502/200 |
| 5,929,275 | A | * | 7/1999  | Wada et al. ................. 562/545 |
| 5,959,143 | A | * | 9/1999  | Sugi et al. .................. 562/534 |
| 6,028,220 | A | * | 2/2000  | Wada et al. ................. 562/546 |

FOREIGN PATENT DOCUMENTS

| EP | 0 051 348 | 5/1982 |
| EP | 0 442 517 | 8/1991 |
| JP | 9-313943  | 12/1997 |

* cited by examiner

*Primary Examiner*—Mark L. Bell
*Assistant Examiner*—Patricia L. Hailey
(74) *Attorney, Agent, or Firm*—Nields & Lemack

(57) ABSTRACT

The present invention relates to a catalyst for producing methacrylic acid by the vapor-phase catalytic oxidation of methacrolein, comprising Mo, V, P and Cu as the indispensable active components, wherein copper acetate is used for all or a part of the necessary amount of a material for said Cu, a coated catalyst and a method for manufacturing the coated catalyst, and methacrolein is reacted in a high conversion and methacrylic acid is produced in a high selectivity by use of the catalyst of the present invention, and the catalyst can be used for reaction under high loading condition.

11 Claims, No Drawings

CATALYST FOR METHACRYLIC ACID PRODUCTION, COATED CATALYST, AND PROCESS FOR PRODUCING THE SAME

TECHNICAL FIELD

The present invention relates to a catalyst for producing methacrylic acid by the vapor-phase catalytic oxidation of methacrolein that has a long life, a high activity and a high selectivity; and the method for manufacturing the catalyst.

BACKGROUND ART

For the production of methacrylic acid by vapor-phase catalytic oxidation of methacrolein, there have been proposed lots of catalysts, most of which contain molybdenum and phosphorus as the main components and have a structure of heteropolyacid and/or the salt thereof. However, they have a low reactivity, a low selection for the object material, and a short life in comparison with the molybdenum-vanadium catalyst proposed for producing acrylic acid by the oxidation of acrolein which is known to be similar to the vapor-phase catalytic oxidation of methacrolein. The proposed catalysts are demanded to improve in catalytic ability though some of them are industrialized.

The present inventors having been trying to improve a low reactive, low selective and short-life catalyst for vapor-phase catalytic oxidation of methacrolein, and found out the catalyst which has high reactivity, high selectivity and good stability in life containing the various elements in addition to Mo, V and P and having a structure of heteropolyacid (or the salt thereof). As a result, there have been proposed the catalysts as described in JP No.11416/1883, JP No.24140/1884, JP No.14535/1987 and JP No.30177/1987.

The catalyst, if packed in a fixed bed reaction vessel for industrial use, has to be molded into a specified size in order to reduce the loss in gas pressure in the catalyst layer. So, it is known that the catalyst powder is generally molded into a pellet, a tablet, a ring and a sphere, or the catalytically active materials are impregnated into or coated on an inactive carrier.

The coated catalyst having the inactive carrier as the core includes the following merits:
(1) The effective utility of the catalytically active component increases.
(2) The improvement in the selectivity can be expected because the staying-time distribution of reaction materials within the catalyst becomes uniform.
(3) An increased thermal conductivity of the catalyst or a dilution effect by an inactive carrier makes it easy to remove the reaction heat.

So, the coated catalyst is often applied to a highly exothermal selective oxidation reaction.

On the other hand, the technical difficulties for producing the coated catalyst are as follows:
(1) It is difficult to produce a mechanically strong catalyst because the coat layer is liable to peel or crack.
(2) It is difficult to coat the inactive carrier with a large amount of catalytically active material.
(3) The inclusion of inactive material makes it difficult to prepare a highly active catalyst.

There has been no general technique to solve such problems because of the diversity in property among catalytically active materials. Practically in this state, the problems are solved individually depending on the catalysts.

An object of the present invention is to provide a catalyst for producing methacrylic acid by vapor-phase catalytic oxidation of methacrolein at a high yield and with a high selectivity; and a method for producing thereof.

DISCLOSURE OF THE INVENTION

In order to solve the above problem, the present inventors have tried to improve a conventional low reactive, low selective and short-life catalyst for vapor-phase catalytic oxidation of methacrolein, and found out the catalyst having high reactivity, high selectivity, good stability in life and high performance suitable for an industrial use, when preparing the catalyst i.e. a heteropolyacid and/or the salt thereof containing Mo, V, P and Cu as the indispensable active components and to which copper acetate is added as the cu component. This finding has completed the present invention. Namely the present invention is as follows:

(1) A catalyst for producing methacrylic acid by the vapor-phase catalytic oxidation of methacrolein, wherein copper acetate is used for all or a part of the necessary amount of a Cu material for preparation of the catalyst comprising Mo, V, P and Cu as the indispensable active components.
(2) A catalyst according to the above term (1), wherein all or a part of said copper acetate is a solid copper acetate to mix and not an aqueous solution.
(3) A catalyst according to the above term (2), wherein said catalyst is a mixture of solid copper acetate with a dried product of a slurry containing Mo, V and P.
(4) A catalyst according to any of the above term (1)–(3), further comprising As as the active component.
(5) A catalyst according to any of the above term (1)–(3), wherein the composition of said active components is represented by the following Formula (1),

$$Mo_{10}V_aP_bCu_cAs_dX_eY_fO_g \qquad (1)$$

(wherein, Mo, V, P, Cu, As and O represent molybdenum, vanadium, phosphorus, copper, arsenic and oxygen respectively; X represents at least one element selected from the group consisting of Ag, Mg, Zn, Al, B, Ge, Sn, Pb, Ti, Zr, Sb, Cr, Re, Bi, W, Fe, Co, Ni, Ce and Th; Y represents at least one element selected from the group consisting of K, Rb and Cs; a, b, c, d, e, f and g represent atomic ratios of the respective elements, with $0.1 \leq a \leq 6$, $0.5 \leq b \leq 6$, $0 < c \leq 3$, $0 \leq d \leq 3$, $0 \leq f \leq 1$; g is the ratio determined by the valence and ratio of the other elements than oxygen)

(6) A catalyst according to the above term (5), further comprising As as the active component.

(7) A method for manufacturing a coated catalyst for producing methacrylic acid by the vapor-phase catalytic oxidation of methacrolein, comprising:
(a) a process for mixing copper acetate and compounds containing one or more of Mo, V and P with water to prepare their aqueous solution or their water-based dispersion (hereinafter referred to as the slurry, including the solution and the dispersion);
(b) a process for drying the slurry prepared in the process (a) to obtain a dried slurry;
(c) a process for coating the dried slurry obtained in the process (b) on a carrier with a binder to obtain a coated product; and
(d) a process for calcining the coated product obtained in the process (c),
wherein said binder is at least one selected from the group consisting of water and an organic compound whose boiling point is 150° C. or lower at 1 atm.

(8) A method for manufacturing a coated catalyst for producing methacrylic acid by the vapor-phase catalytic oxidation of methacrolein, comprising:

(a) a process for mixing compounds containing one or more of Mo, V and P with water to prepare their aqueous solution or their water-based dispersion (hereinafter referred to as the slurry, including the solution and the dispersion);

(b) a process for drying the slurry prepared in the process (a) to obtain a dried slurry;

(b') a process for mixing solid copper acetate with the dried slurry obtained in the process (b) to prepare a mixture;

(c) a process for coating the mixture prepared in the process (b') on a carrier with a binder to obtain a coated product; and (d) a process for calcining the coated product obtained in the process (c), wherein said binder is at least one selected from the group consisting of water and an organic compound whose boiling point is 150° C. or lower at 1 atm.

(9) A method for manufacturing a coated catalyst according to the above term (7) or (8), further using a compound containing As used to mix as the raw material to prepare the slurry in the process (a).

(10) A method for manufacturing a coated catalyst according to the above term (7) or (8), further using copper oxide used to mix as the raw material to prepare the slurry in the process (a).

(11) A method for manufacturing a coated catalyst according to the above term (7) or (8), further using a compound containing As and copper oxide used to mix as the raw material to prepare the slurry in the process (a).

(12) A method for manufacturing a coated catalyst according to any of the above term (7)–(11), wherein said binder is ethanol.

(13) A method for manufacturing a coated catalyst according to any of the above term (12), wherein said binder is a mixture having an ethanol/water ratio (mass ratio) of 10/0–5/5.

(14) A coated catalyst obtained by a method according to any of the above term (7)–(13).

(15) A coated catalyst obtained by coating a catalyst comprising Mo, V, P and Cu as the indispensable active components on a carrier, wherein said catalyst is prepared by using copper acetate for all or a part of a Cu material.

(16) The coated catalyst according to claim 15, wherein the catalyst has a structure of heteropolyacid or salt thereof.

BEST MODE FOR CARRYING OUT THE INVENTION

One of the preferable method to obtain a catalyst of the present invention is to dissolve and/or disperse in water the plural compounds (hereinafter referred to as "an active-component-containing compound" instead of "a compound which contains the active components" depending on the cases) containing one or more of Mo, V, P, Cu and other elements if necessary to prepare a slurry (the process (a)), wherein copper acetate is added as a copper compound, followed by drying the slurry (the process (b)). Another is to mix a solid copper acetate (generally, powdery or granular) after drying the slurry, in place of all or a part of copper acetate used in the preparation of the above slurry.

When a compound containing an alkali metal is used as the material for preparing the slurry, catalyst obtained by drying the slurry contains a heteropolyacid salt as the catalytically active component.

For the other active-component-containing compounds used for preparing a slurry in the present invention except copper acetate, the preferable ones are the compounds which can be converted to the heteropolyacid (salt) by drying (the process (b)) or calcining (the process (d)). The compounds include chlorides, sulfates, nitrates, ammonium salts, oxides and acetates of the active elements. The preferable compounds are more specifically exemplified. They include nitrate salts such as potassium nitrate, cobalt nitrate and cesium nitrate; oxides such as molybdenum oxide, vanadium pentaoxide, antimony trioxide, cerium oxide, zinc oxide or germanium oxide; and an acid (or the salt) such as orthophosphoric acid, phosphoric acid, arsenic acid, boric acid, aluminium phosphate or 12 tungustophosphoric acid. These may be used alone or in combination of two or more.

The ammonium salt, whose ammonium group is a part of catalytically active component to contribute in catalytic activity, however, needs to be used carefully because it may shorten the reaction stability of the prepared catalyst. Other compounds than the ammonium salts are generally used.

For a compound containing Cu (hereinafter referred to as a copper compound) in the present invention, copper acetate may be used in all or a part of the amount necessary for the copper compound to be a catalyst. The reason is not clear why the catalytic ability is excellent when copper acetate is used. But it is assumed that the copper acetate has an effect to derive reduction state of the active components for preparing the heteropolyacid (salt) into the optimum state. The copper acetate is not limited to either the hydride salt or the anhydrous salt, and any of cuprous acetate, cupric acetate and basic copper acetate can be used. A bivalent copper compound, especially cupric acetate is preferable. As long as copper acetate is used as a copper compound, the combination with other copper compounds brings out no problem and rather, if used in combination with copper oxide, especially with cupric oxide, a good result can be obtained in some cases. The combination of copper acetate with the other copper compound can be used with no limitation if the sum of their coppers has generally an atomic ratio of more than 0 and 3 or less, preferably 0.01 or more and 1 or less relative to the molybdenum atomic ratio of 10. It is preferable that the ratio of copper atom in the copper acetate to that in the other copper compound is 25:100–100:0

The copper acetate used in the present invention may be added with other active-component-containing compounds to prepare the slurry. Alternatively, a necessary amount of solid copper acetate without making an aqueous solution preferably in the form of powder or granule, may be added to the dried slurry (preferably powder or granule) (the process (b')). The latter way may be combined with the former way depending on the cases. For example, a part of copper acetate is used as a material for the slurry and the remainder, as a solid copper acetate, can be added to the dried slurry. In the latter way, it is preferable that the ratio of the copper acetate added as the material for the slurry to the solid copper acetate mixed with the dried slurry is 0:100–100:25. The solid copper acetate is not limited to a specific shape or size as far as it can be uniformly mixed with the dried slurry. But it is better to use the similar size particles so as to make it easy to mix uniformly. It is preferably granular or powdery, more preferably powdery. A granule or powder of solid copper acetate has generally a particle size of 2 mm or less, preferably 1 mm or less, more preferably 500 $\mu$m or less and most preferably 300 $\mu$m or less. The lower limit is not specified, but is generally 10 or more and preferably 30 or more because there is no particular merit it is too fine.

The latter way, namely to add the solid copper acetate to the dried slurry, is more preferable. The catalyst manufactured by the latter way shows higher activity than what is obtained by the former way in which all copper acetate are used as the material for the slurry. When the latter catalyst is used to produce methacrylic acid from methacrolein, a higher yield (with a higher conversion and a nearly the same selectivity) at the same reaction temperature can be obtained compared with the case the former catalyst is used. In other words, the same yield (the same conversion and the same selectivity) can be obtained at a lower reaction temperature. A lower temperature is very preferable for the catalyst life.

The other active component than Mo, V, P and Cu in the present invention includes As, Ag, Mg, Zn, Al, B, Ge, Sn, Pb, Ti, Zr, Sb, Cr, Re, Bi, W, Fe, Co, Ni, Ce, Th, K, Rb and Cs. The preferable component is one or more elements selected from the group consisting of As, Ag, Mg, Zn, Al, B, Ge, Sn, Pb, Ti, Zr, Sb, Cr, Re, Bi, W, Fe, Co, Ni, Ce, Th, K, Rb and Cs. As is especially preferable. In some cases, it gives a favorable results if As is used in combination with the Cs both as an active component.

The atomic ratio of each active component of the catalyst in the present invention, if the molybdenum has an atomic ratio of 10, is as follows:

The vanadium has generally that of 0.1 or more and 6 or less, preferably 0.3 or more and 2.0 or less;

The phosphorus has generally that of 0.5 or more and 6 or less, preferably 0.5 or more and 3 or less;

The copper has generally that of more than 0 and 3 or less, preferably 0.01 or more and 1 or less.

The other active component used for the catalyst if necessary and its ratio can be determined depending on the using conditions in order to show an optimal performance. The preferable catalyst used under a common condition has an active component composition represented by Formula (1) below:

$$Mo_{10}V_aP_bCu_cAs_dX_eY_fO_g \tag{1}$$

(wherein, Mo, V, P, Cu, As and O represent molybdenum, vanadium, phosphorus, copper, arsenic and oxygen respectively; X represents at least one element selected from the group consisting of Ag, Mg, Zn, Al, B, Ge, Sn, Pb, Ti, Zr, Sb, Cr, Re, Bi, W, Fe, Co, Ni, Ce and Th; Y represents at least one element selected from the group consisting of K, Rb and Cs; a, b, c, d, e, f and g represent atomic ratios of their respective elements, with $0.1 \leq a \leq 6$, preferably $0.3 \leq a \leq 2$; $0.5 \leq b \leq 6$, preferably $0.5 \leq b \leq 3$; $0 \leq c \leq 3$, preferably $0.01 < c \leq 1$; $0 \leq d \leq 3$, preferably $0.01 \leq d \leq 1$; $0 \leq e \leq 3$, preferably $0.01 \leq e \leq 1$; $0 \leq f \leq 1$, preferably $0 \leq f \leq 0.06$; g is the ratio determined by the valence and ratio of the other elements than oxygen, generally with $35 \leq g \leq 80$).

This catalyst can be obtained by the following procedure. A slurry solution of active-component-containing compounds is prepared at first. Plural compounds containing each active component (s) can be uniformly mixed with a solvent, preferably with water to prepare the slurry solution. The slurry solution contains preferably all the necessary active component-containing compounds excluding a copper compound in their respective amounts necessary for the catalyst. The slurry solution may contain the copper compound in no amount, in a part of the necessary amount, or in whole the necessary amount.

The copper compound also may be added with the other compounds to prepare the slurry that contains all the active-component-containing compounds necessary for the catalyst of the present invention. When the slurry containing the copper compound is prepared, copper acetate is used either in all the necessary amount or in part of the copper compound. Copper acetate maybe used to prepare the slurry that contains the copper compound in part of the necessary amount, or other copper compounds without copper acetate may be used depending on the contents' amount. If the slurry contains the copper compound in no amount or only in part of the necessary amount, the shortage have to be supplemented with the solid copper acetate after drying the slurry as being described later.

The slurry in the present invention is preferably an aqueous solution. The ratio among the active-component-containing compounds to use is not limited if their respective atomic ratios are within the above ranges. The amount of water to use is not limited if it allows all the compounds to be completely dissolved or uniformly mixed, and can be determined due to the consideration of the drying method and the drying condition shown below. It is generally 200–2,000 parts by mass relative to 100 parts by mass of total amount of the compounds for preparing the slurry. However, too much water brings about many demerits such as a high energy cost for drying process or an incomplete drying. There brings little merits. Therefore appropriate amount of water is preferable.

The slurry thus obtained is dried to change into the dried slurry. The drying method is not limited provided that it can completely dry the slurry, and includes drum drying, freeze-drying and spray drying. The spray drying is preferable in the present invention because it can dry the slurry into a powder or a granule faster than the others.

The drying temperature varies depending on the concentration and the flow speed of the slurry, and is commonly 85–130° C. at the outlet of a drier. The slurry is preferably dried into the particle of which average size is 30–150 $\mu$m. The dried slurry, if it is a block or a large particle, is preferably ground to get a particle having the above size. The dried slurry in the present invention includes the above particle obtained by grinding.

If the slurry contains the copper compound in no amount or in only a part of the necessary amount, copper acetate is supplemented to the dried slurry in the amount to cover the shortage to have a homogeneous mixture. The dried slurry or the above copper acetate mixture (hereinafter inclusively referred to as a dried slurry) can directly apply to the vapor-phase catalytic oxidation, but is preferably molded into a pellet, a tablet, a ring and a sphere in order to reduce the loss in reaction gas pressure as described above. It is especially desirable that the dried slurry is coated on an inert carrier to prepare a coated catalyst, because the catalyst is expected to have an increased selection and remove a reaction heat.

The coating process (the process (c)) is preferably a tumbling granulation as described below. An apparatus for this method has a flat or uneven disk set on the bottom of a fixed vessel. The high speed rotation of the disk causes a carrier to repeat its revolving movement and orbital movement, vigorously stirring in the vessel. The mixture of a binder, the dried slurry and other additives such as a molding auxiliary and a strength improvement agent are added to the carrier to be coated with the mixture. The method for adding the binder includes: (1) the binder beforehand is mixed in the mixture; (2) the binder is added simultaneously with the mixture in the fixed vessel; (3) the binder is added succeedingly after the mixture added into the fixed vessel; (4) the binder is added before the mixture added into the fixed vessel; (5) the mixture and the binder separated into their respective portions, which are added in the appropriate combination of (2)–(4) to reach their total amount. The binder can be added optionally by any of these methods.

For the (5) method, an automatic feeder is preferably used to regulate the adding speed so as to prevent the mixture from adhering to the wall of the fixed vessel and from mutually agglomerating, and the mixture to be supported on the carrier in the prescribed amount.

The binder is not limited to a special one as long as at least one binder is selected from the group consisting of water and an organic solvent having a boiling point of 150° C. or lower at 1 atm. But it is preferable that a binder have a boiling point of 100° C. or lower considering the drying procedure after coating. The other binder than water includes an alcohol such as methanol, ethanol, propanols and butanols, preferably a C1–C4 alcohol; an ether such as ethyl ether, butyl ether and dioxane; an ester such as ethyl acetate and butyl acetate; a ketone such as acetone and methyl ethyl ketone; and these aqueous solutions. Ethanol is especially preferable. Ethanol as the binder has an ethanol/water ratio of 10/0–5/5(by mass), preferably of 10/0–7/3(by mass). These binders are generally used in 2–60 parts by mass, preferably 5–25 parts by mass relative to 100 parts by mass of the dried slurry.

The carrier to use in the present invention includes concretely a spherical carrier having generally a diameter of 1–15 mm, preferably 2.5–10 mm such as silicone carbide, alumina, mullite and alundum. These carriers have generally a hole fraction of 10–70%. The carrier and the dried slurry to coat are generally used in a ratio of (dried slurry)/(dried slurry+carrier)=10–75% by mass, preferably 15–60% by mass.

The coated catalyst, if the dried slurry has a higher ratio, is inclined to have a smaller mechanical strength (resulting in a larger attrition), though is higher the reaction activity. Contrarily, the coated catalyst, if the dried slurry has a lower ratio to use, is inclined to have a smaller reaction activity, though is larger the mechanical strength (resulting in a smaller attrition).

The dried slurry may be coated on the carrier in the present invention with a molding auxiliary such as silica gel, diatomaceous earth and an alumina powder if necessary. The molding auxiliary is generally used in an amount of 5–60 parts by mass relative to 100 parts by mass of the dried slurry.

It is useful for increasing the mechanical strength of the catalyst to use an inorganic fiber such as a ceramic fiber and a whisker if necessary as the strength improvement agent, which is inert to the catalytic components. But a fiber such as a potassium titanate whisker and a basic magnesium carbonate whisker are not preferable because they are reactive with the catalytic components. The fiber is generally used in an amount of 1–30 parts by mass relative to 100 parts by mass of the dried slurry.

An additive such as the above molding auxiliary and the strength improvement agent are generally added into a granulator together with the carrier, the dried slurry and the binder for coating the carrier in the coating process.

The dried slurry thus obtained is used for coating the carrier. The coated product thus obtained has generally a diameter of 3–15 mm.

The coated catalyst thus obtained, which can be directly used as the catalyst for the vapor-phase catalytic oxidation, is preferably calcined to have an increased catalytic activity. The calcining temperature is generally 100–420° C., preferably 250–400% and the calcining time is 1–20 hours.

The catalyst thus obtained of the present invention is used for preparing methacrylic acid by the vapor-phase catalytic oxidation of methacrolein. The phrase "the catalyst of the present invention" is used to mean, unless otherwise specified, that it includes both a dried slurry obtained through the processes (a)–(b) and the process (b') if necessary and a coated catalyst obtained through the process (c) (and preferably the process (d)).

The molecular oxygen or a molecular oxygen-containing gas is used for the vapor-phase catalytic oxidation. The molecular oxygen is preferably used in a mol ratio of 0.5–20, more preferably 1–10 to the methacrolein. Water is preferably added in the raw material gas in a mol ratio of 1–20 to the methacrolein in order to accelerate the smooth reaction.

The raw material gas may contain, in addition to oxygen and, if necessary, water (generally water vapor), gas such as nitrogen, carbon dioxide and a saturated hydrocarbon inert to the reaction.

A gas obtained by the oxidation of isobutylene and tertiary butanol may be supplied for the methacroleine.

The reaction temperature of the vapor-phase catalytic oxidation is generally 200–400%, preferably 260–360%. The space velocity (SV) for supplying the raw material gas is generally 100–6,000 hr $r^{-1}$, preferably 400–3,000 h $r^{-1}$.

The catalyst of the present invention allows the reaction to be executed at a high space velocity, because it does not give a large change in reaction yield at an increased SV.

The vapor-phase catalytic oxidation can be executed under a pressure or under a reduced pressure. A pressure around the atmosphere is suitable for the oxidation.

EXAMPLE

The following examples are further illustrative of the present invention. Any of the ratios of the active component compositions in the Examples are calculated from an amount of materials used in the Examples and the formula shows except oxygen.

Example A1

(1) Preparation of Catalyst

In 1900 ml of pure water, 300 g of molybdenum trioxide, 11.37 g of vanadium pentaoxide, 3.31 g of cupric oxide, 8.32 g of cupric acetate monohydrate, 28.82 g of 85% orthophosphoric acid and 24.64 g of 60% arsenic acid were dispersed or dissolved and then stirred to heat under reflux at 95–100° C. for about 6 hours to obtain a reddish brown transparent solution.

Antimony trioxide (1.52 g) was added in the above solution and then heated under reflux at 95–100° C. for about 3 hours to obtain a navy blue solution.

Then, the solution was dried by a spray drier to obtain a catalyst granule. The catalyst granule (319 g) was mixed uniformly with 44.7 g of ceramic fiber to get a powder, which was then gradually sprinkled over 300 g of a spherical porous alumina carrier under dropping 90% aqueous ethanol solution in a rotary drum to coat the spherical carrier with the catalyst granule. Almost no lost powder was perceived during the process.

The molded product thus obtained was calcined at 310° C. for 5 hours under an air stream to obtain a coated catalyst. The coated catalyst had an active component composition of $Mo_{10}V_{0.6}P_{1.2}Cu_{0.4}As_{0.5}Sb_{0.05}$.

(2) Catalytic Oxidation of Methacrolein

The reacting catalyst (10 ml) thus obtained was packed in a stainless steel reactor tube having an inner diameter of 18.4 mm, in which methacrolein was oxidized under the condition that the gas composition of raw materials was methacrolein: oxygen: water vapor:nitrogen=1:2.8:5.0:21.0 (molar ratio); the space velocity (SV) was 1,000 h $r^{-4}$ and the reaction temperature was 310° C. Methacrolein conversion was 85.9% and selectivity to methacrylic acid was 84.8%.

Comparative Example 1

In 1900 ml of pure water, 300 g of molybdenum trioxide, 11.37 g of vanadium pentaoxide, 6.63 g of cupric oxide, 28.82 g of 85% orthophosphoric acid and 24.64 g of 60% arsenic acid were dispersed or dissolved and then stirred to heat under reflux at 95–100° C. for 6 hours to obtain a reddish brown transparent solution.

In the above solution, 1.52 g of antimony trioxide was added and then heated under reflux at 95–100° C. for 3 hours to obtain a navy blue solution.

Then, the solution was dried by a spray drier to obtain a catalyst granule.

The succeeding procedures were done as in Example A1 to obtain a coated catalyst. The coated catalyst thus obtained had an active component composition of $Mo_{10}V_{0.6}P_{1.2}Cu_{0.4}As_{0.5}Sb_{0.05}$.

The coated catalyst thus obtained was used for the same reaction as Example A1. Methacrolein conversion was 79.9% and selectivity to methacrylic acid was 87.8%.

Example A2

In 1900 ml of pure water, 300 g of molybdenum trioxide, 24.64 g of vanadium pentaoxide, 8.32 g of cupric acetate monohydrate, 26.42 g of 85% orthophosphoric acid and 9.22 g of rubidium nitrate were dispersed or dissolved and then stirred to heat under reflux at 95–100° C. for about 9 hours to obtain a reddish brown transparent solution.

Then, the solution was dried by a spray drier to obtain a catalyst granule.

The succeeding procedures were done as in Example A1 to obtain a coated catalyst. The coated catalyst thus obtained had an active component composition of $Mo_{10}V_{1.3}P_{1.1}Cu_{0.2}Rb_{0.3}$.

The coated catalyst thus obtained was used for the same reaction as Example A1. Methacrolein conversion was 74.2% and selectivity to methacrylic acid was 79.0%.

Comparative Example 2

In 1900 ml of pure water, 300 g of molybdenum trioxide, 24.64 g of vanadium pentaoxide, 3.31 g of cupric oxide, 26.42 g of 85% orthophosphoric acid and 9.22 g of rubidium nitrate were dispersed or dissolved and then stirred to heat under reflux at 95–100° C. for 9 hours to obtain a reddish brown transparent solution. Then, the solution was dried by a spray drier to obtain a catalyst granule.

The succeeding procedures were done as in Example A1 to obtain a coated catalyst. The coated catalyst thus obtained had an active component composition of $Mo_{10}V_{1.3}P_{1.1}Cu_{0.2}Rb_{0.3}$.

The coated catalyst thus obtained was used for the same reaction as Example A1. Methacrolein conversion was 71.7% and selectivity to methacrylic acid was 79.7%.

Example A3

A coated catalyst was prepared by the same procedures as in Example A1, except that 3.59 g of cerium oxide were used in place of antimony trioxide.

The coated catalyst thus obtained had an active component composition of $Mo_{10}V_{0.6}P_{1.2}Cu_{0.4}As_{0.5}Ce_{0.1}$.

Then, the coated catalyst thus obtained was used for the same reaction as Example A1. Methacrolein conversion was 85.2% and selectivity to methacrylic acid was 84.0%.

Example A4

A coated catalyst was prepared by the same procedures as in Example A1, except that 8.32 g were changed to 16.64 g in cupric acetate monohydrate, 3.31 g were changed to 0 g in cupric oxide, and 1.66 g of ferric oxide was used in place of antimony trioxide.

The coated catalyst thus obtained had an active component composition of $Mo_{10}V_{0.6}P_{1.2}Cu_{0.4}As_{0.5}Fe_{0.1}$.

Then, the coated catalyst thus obtained was used for the same reaction as Example A1. Methacrolein conversion was 86.0% and selectivity to methacrylic acid was 85.0%.

Example A5

A coated catalyst was prepared by the same procedures as in Example A1, except that 8.32 g were changed to 12.48 g in cupric acetate monohydrate, 3.31 g were changed to 1.66 g in cupric oxide, 28.82 g were changed to 27.62 g in 85% orthophosphoric acid and 5.62 g of 12 phosphotungstic acid were used in place of antimony trioxide.

The coated catalyst thus obtained had an active component composition of $Mo_{10}V_{0.6}P_{1.2}Cu_{0.4}As_{0.5}W_{0.1}$.

Then, the coated catalyst thus obtained was used for the same reaction as Example A1. Methacrolein conversion was 85.0% and selectivity to methacrylic acid was 84.5%.

Example A6

A coated catalyst was prepared by the same procedures as in Example A1, except that 24.64 g were changed to 19.71 g in 60% arsenic acid, and 2.11 g of potassium nitrate was used in place of antimony trioxide.

The coated catalyst thus obtained had an active component composition of $Mo_{10}V_{0.6}P_{1.2}Cu_{0.4}As_{0.4}K_{0.1}$.

Then, the coated catalyst thus obtained was used for the same reaction as Example A1. Methacrolein conversion was 82.3% and selectivity to methacrylic acid was 84.5%.

Example A7

A coated catalyst was prepared by the same procedures as in Example A1, except that 24.64 g were changed to 19.71 g in 60% arsenic acid, and 3.14 g of tin oxide and 4.06 g of cesium nitrate were used in place of antimony trioxide.

The coated catalyst thus obtained had an active component composition of $Mo_{10}V_{0.6}P_{1.2}Cu_{0.4}As_{0.4}Sn_{0.1}Cs_{0.1}$.

Then, the coated catalyst thus obtained was used for the same reaction as Example A1. Methacrolein conversion was 82.4% and selectivity to methacrylic acid was 85.7%.

Example A8

In 1900 ml of pure water, 300 g of molybdenum trioxide, 24.64 g of vanadium pentaoxide, 8.32 g of cupric acetate monohydrate, 24.02 g of 85% orthophosphoric acid and 12.18 g of cesium nitrate were dispersed or dissolved and then stirred to heat under reflux at 95–100° C. for about 9 hours to obtain a reddish brown transparent solution.

Then, the solution was dried by a spray drier to obtain a catalyst granule.

A coated catalyst was prepared by the same procedures as in Example A1.

The coated catalyst thus obtained had an active component composition of $Mo_{10}V_{1.3}P_{1.0}Cu_{0.4}Cs_{0.3}$.

Then, the coated catalyst thus obtained was used for the same reaction as Example A1. Methacrolein conversion was 75.3% and selectivity to methacrylic acid was 79.0%.

Example A9

In 1900 ml of pure water, 300 g of molybdenum trioxide, 22.74 g of vanadium pentaoxide, 8.32 g of cupric acetate monohydrate, and 26.42 g of 85% orthophosphoric acid were dispersed or dissolved and then stirred to heat under reflux at 95–100° C. for about 6 hours to obtain a reddish brown transparent solution. To the above solution was added 1.09 g of germanium oxide and then heated under reflux at 95–100° C. for about 3 hours to obtain a reddish brown solution.

Then, the solution was dried by a spray drier to obtain a catalyst granule. The catalyst granule (319 g) was mixed uniformly with 44.7 g of ceramic fiber to get a powder, which was then gradually sprinkled over 300 g of a spherical porous alumina carrier under dropping 70% aqueous ethanol solution in a rotary drum to coat the spherical carrier with the catalyst granule.

The molded product thus obtained was calcined at 310° C. for 5 hours under an air stream to obtain a coated catalyst. The coated catalyst had an active component composition of $Mo_{10}V_{1.2}P_{1.1}Cu_{0.2}Ge_{0.05}$.

Then, the coated catalyst thus obtained was used for the same reaction as Example A1. Methacrolein conversion was 73.2% and selectivity to methacrylic acid was 77.8%.

Example A10

A coated catalyst was prepared by the same procedures as in Example A9, except that 1.95 g of gallium oxide were used in place of germanium oxide in the Example A9.

The coated catalyst thus obtained had an active component composition of $Mo_{10}V_{1.2}P_{1.1}Cu_{0.2}Ga_{0.1}$.

Then, the coated catalyst thus obtained was used for the same reaction as Example A1. Methacrolein conversion was 75.9% and selectivity to methacrylic acid was 74.9%.

Example A11

In 1900 ml of pure water, 300 g of molybdenum trioxide, 24.64 g of vanadium pentaoxide, 16.64 g of cupric acetate monohydrate, 3.31 g of cupric oxide and 36.03 g of 85% orthophosphoric acid were dispersed or dissolved and then stirred to heat under reflux at 95–100° C. for about 6 hours to obtain a reddish brown transparent solution.

To the above solution was added 2.58 g of diboron trioxide and then heated under reflux at 95–100° C. for about 3 hours to obtain a reddish brown solution.

Then, the solution was dried by a spray drier to obtain catalyst granules. The catalyst granules (319 g) was mixed uniformly with 44.7 g of ceramic fiber to get a powder, which was then gradually sprinkled over 300 g of a spherical porous alumina carrier under dropping 90% aqueous ethanol solution in a rotary drum to coat the spherical carrier with the catalyst granules.

The molded product thus obtained was calcined at 310° C. for 5 hours under an air stream to obtain a coated catalyst. The coated catalyst had an active component composition of $Mo_{10}V_{1.3}P_{1.5}Cu_{0.6}B_{0.2}$.

Then, the coated catalyst thus obtained was used for the same reaction as Example A1. Methacrolein conversion was 81.2% and selectivity to methacrylic acid was 78.0%.

Example A12

A coated catalyst was prepared by the same procedures as in Example A11, except that 10.11 g of bismuth nitrate were used in place of 2.58 g of diboron trioxide in the Example A11.

The coated catalyst thus obtained had an active component composition of $Mo_{10}V_{1.3}P_{1.5}Cu_{0.6}Bi_{0.01}$.

Then, the coated catalyst thus obtained was used for the same reaction as Example A1. Methacrolein conversion was 79.3% and selectivity to methacrylic acid was 78.5%.

Example A13

In 1900 ml of pure water, 300 g of molybdenum trioxide, 24.64 g of vanadium pentaoxide, 12.48 g of cupric acetate monohydrate, 1.16 g of cupric oxide and 31.22 g of 85% orthophosphoric acid were dispersed or dissolved and then stirred to heat under reflux at 95–100° C. for about 5 hours to obtain a reddish brown transparent solution.

To the above solution was added 0.33 g of ferric oxide, 0.61 g of antimony trioxide, 0.72 of ceric oxide, 2.03 g of cesium nitrate and then heated under reflux at 95–100° C. for about 5 hours to obtain a reddish brown solution.

Then, the solution was dried by a spray drier to obtain catalyst granules. The catalyst granules (319 g) was mixed uniformly with 44.7 g of ceramic fiber to get a powder, which was then gradually sprinkled over 300 g of a spherical porous alumina carrier under dropping 90% aqueous ethanol solution in a rotary drum to coat the spherical carrier with the catalyst granules.

The molded product thus obtained was calcined at 310° C. for 5 hours under an air stream to obtain a coated catalyst. The coated catalyst had an active component composition of $Mo_{10}V_{1.3}P_{1.3}Cu_{0.4}Fe_{0.02}Sb_{0.02}Ce_{0.02}Cs_{0.05}$.

Then, the coated catalyst thus obtained was used for the same reaction as Example A1. Methacrolein conversion was 80.3% and selectivity to methacrylic acid was 79.2%.

Example A14

In 1900 ml of pure water, 300 g of molybdenum trioxide, 24.64 g of vanadium pentaoxide, 16.64 g of cupric acetate monohydrate, 3.31 g of cupric oxide and 36.03 g of 85% orthophosphoric acid were dispersed or dissolved and then stirred to heat under reflux at 95–100° C. for about 6 hours to obtain a reddish brown transparent solution.

To the above solution was added 39.11 g of antimony trioxide, 20.30 g of cesium nitrate and then heated under reflux at 95–100° C. for about 5 hours to obtain a navy blue solution.

Then, the solution was dried by a spray drier to obtain catalyst granules. The catalyst granules (319 g) was mixed uniformly with 44.7 g of ceramic fiber to get a powder, which was then gradually sprinkled over 300 g of a spherical porous alumina carrier under dropping 90% aqueous ethanol solution in a rotary drum to coat the spherical carrier with the catalyst granules.

The molded product thus obtained was calcined at 310° C. for 5 hours under an air stream to obtain a coated catalyst. The coated catalyst had an active component composition of $Mo_{10}V_{1.3}P_{1.5}Cu_{0.6}Sb_{0.3}Cs_{0.5}$.

Then, the coated catalyst thus obtained was used for the same reaction as Example A1 except that the reaction temperature was changed to 320° C. Methacrolein conversion was 80.6% and selectivity to methacrylic acid was 78.8%.

Example B1

(1) Preparation of Catalyst

In 1900 ml of pure water, 300 g of molybdenum trioxide, 11.37 g of vanadium pentaoxide, 3.31 g of cupric oxide, 28.82 g of 85% orthophosphoric acid and 24.64 g of 60% arsenic acid were dispersed or dissolved and then stirred to heat under reflux at 95–100° C. for about 6 hours to obtain a reddish brown transparent solution.

To the above solution was added 1.52 g of antimony trioxide and then heated under reflux at 95–100° C. for about 3 hours to obtain a navy blue solution.

Then, the solution was dried by a spray drier to obtain catalyst granules. The catalyst granules 316 g was mixed uniformly with 7.64 g of solid cupric acetate monohyrate for allowing a Cu/Mo atomic ratio of 0.2/10 and 44.7 g of ceramic fiber to get a mixed powder. The mixed powder was then gradually sprinkled over 300 g of a spherical porous alumina carrier prepared in a rotary drum under dropping 90% aqueous ethanol solution to coat the spherical carrier with the catalytically active component. Almost no lost powder was perceived during the process.

The molded product thus obtained was calcined at 310° C. for 5 hours under an air stream to obtain a coated catalyst of the present invention. The coated catalyst had an active component composition of $Mo_{10}V_{0.6}P_{1.2}Cu_{0.4}As_{0.5}Sb_{0.05}$.

(2) Catalytic Oxidation of Methacrolein

The coated catalyst 10 ml thus obtained were packed in a stainless steel reactor tube having an inner diameter of 18.4 mm, in which methacrolein was oxidized at a condition that the gas composition (molar ratio) of raw materials was methacrolein:oxygen:water vapor:nitrogen=1:2.8:5.0:21.0; the space velocity (SV) was 1,000 h $r^{-1}$ and the reaction temperature was 310° C. Methacrolein conversion was 88.8% and selectivity to methacrylic acid was 84.5%.

Example B2

A coated catalyst was prepared by the same procedures as in Example B1, except that 11.37 g were changed to 13.26 g in vanadium pentaoxide, 3.31 g were changed to 4.96 g in cupric oxide, 28.82 g were changed to 31.22 g in 85% orthophosphoric acid, 1.52 g was changed to 3.04 g in antimony trioxide, and 7.64 g were changed to 3.75 g in solid cupric acetate monohydrate.

The coated catalyst thus obtained had an active component composition of $Mo_{10}V_{0.7}P_{1.3}Cu_{0.4}As_{0.5}Sb_{0.1}$.

Then, the coated catalyst thus obtained was used for the same reaction as Example B1. Methacrolein conversion was 84.4% and selectivity to methacrylic acid was 86.7%.

Example B3

In 1900 ml of pure water, 300 g of molybdenum trioxide, 24.64 g of vanadium pentaoxide, and 40.83 g of 85% orthophosphoric acid were dispersed or dissolved and then stirred to heat under reflux at 95–100° C. for 6 hours, followed by adding 8.42 g of potassium nitrate and heating under reflux for 3 hours to obtain a reddish brown solution. The solution was dried by a spray drier to obtain granules which were ground in a mortar into 24 mesh or less to get a powder. The powder 310 g were mixed uniformly with 21.87 g of solid cupric acetate monohydrate for allowing a Cu/Mo atomic ratio of 0.6/10 and 44.7 g of ceramic fiber to get a mixed powder. The mixed powder was then gradually sprinkled over 300 g of a spherical porous alumina carrier under dropping 90% aqueous ethanol solution in a rotary drum to coat the spherical carrier with the catalytically active component composition. Almost no lost powder was perceived during the process.

The molded product thus obtained was calcined at 310° C. for 5 hours under an air stream to obtain a coated catalyst of the present invention. The coated catalyst had an active component composition of $Mo_{10}V_{1.3}P_{1.7}Cu_{0.6}K_{0.4}$.

Then, the coated catalyst thus obtained was used for the same reaction as Example B1. Methacrolein conversion was 85.9% and selectivity to methacrylic acid was 73.8%.

Example B4

A coated catalyst was prepared by the same procedures as in Example B1, except that 3.39 g of cerium oxide was used in place of antimony trioxide, and 7.64 g were changed to 7.59 g in solid cupric acetate monohydrate.

The coated catalyst thus obtained had an active component composition of $Mo_{10}V_{0.6}P_{1.2}Cu_{0.4}As_{0.5}Ce_{0.1}$.

Then, the coated catalyst thus obtained was used for the same reaction as Example B1, except that the reaction temperature was changed to 305° C. Methacrolein conversion was 85.9% and selectivity to methacrylic acid was 84.6%.

Example B5

A coated catalyst was prepared by the same procedures as in Example B1, except that 1.70 g of zinc oxide was used in place of antimony trioxide, and 1.66 g of cupric oxide and 4.16 g of solid cupric acetate monohydrate were used as the copper compound which is added for preparing a slurry solution in place of 3.31 g of cupric oxide.

The coated catalyst thus obtained had an active component composition of $Mo_{10}V_{0.6}P_{1.2}Cu_{0.4}As_{0.5}Zn_{0.1}$.

Then, the coated catalyst thus obtained was used for the same reaction as Example B1, except that the reaction temperature was changed to 305° C. Methacrolein conversion was 80.5% and selectivity to methacrylic acid was 85.0%.

Example B6

A coated catalyst was prepared by the same procedures as in Example B1, except that 5.90 g of cobalt nitrate was used in place of antimony trioxide, 11.37 g was changed to 13.27 g in vanadium pentaoxide, and 31.22 g was changed to 26.42 g in 85% orthophosphoric acid.

The coated catalyst thus obtained had an active component composition of $Mo_{10}V_{0.7}P_{1.1}Cu_{0.4}As_{0.5}Co_{0.1}$.

Then, the coated catalyst thus obtained was used for the same reaction as Example B1. Methacrolein conversion was 87.2% and selectivity to methacrylic acid was 84.8%.

Example B7

A coated catalyst of the present invention was prepared by the same procedures as in Example B6, except that 2.54 g of aluminium phosphate was used in place of cobalt nitrate and 26.42 g was changed to 24.02 g in 85% orthophosphoric acid.

The coated catalyst thus obtained had an active component composition of $Mo_{10}V_{0.7}P_{1.1}Cu_{0.4}As_{0.5}Al_{0.1}$.

Then, the coated catalyst thus obtained was used for the same reaction as Example B1. Methacrolein conversion was 86.8% and selectivity to methacrylic acid was 85.2%.

Example B8

A coated catalyst of the present invention was prepared by the same procedures as in Example B6, except that 7.73 g of boric acid and 35.73 g of 12-tungstophosphoric acid were used in place of cobalt nitrate, 26.42 g was changed to 25.22 g in 85% orthophosphoric acid, 3.31 g was changed to 0 g in cupric oxide, and 7.63 g was changed to 14.09 g in solid cupric acetate monohydrate.

The coated catalyst thus obtained had an active component composition of $Mo_{10}V_{0.7}P_{1.1}Cu_{0.4}As_{0.5}B_{0.6}W_{0.6}$.

The coated catalyst thus obtained was used for the same reaction as Example B1. Methacrolein conversion was 87.3% and selectivity to methacrylic acid was 85.9%.

Example B9

In 1900 ml of pure water, 300 g of molybdenum trioxide, 22.74 g of vanadium pentaoxide, 3.31 g of cupric oxide, 28.63 g of 85% orthophosphoric acid were dispersed or dissolved and then stirred to heat under reflux at 95–100° C. for about 6 hours to obtain a reddish brown transparent solution.

To the above solution was added 5.62 g of 12-tungstophosphoric acid and then further heated under reflux at 95–100° C. for about 3 hours.

Then, the solution was dried by a spray drier to obtain catalyst granules. The catalyst granules 316 g was mixed uniformly with 7.54 g of solid cupric acetate monohyrate for allowing a Cu/Mo atomic ratio of 0.2/10 and 44.7 g of ceramic fiber to get a mixed powder. The mixed powder was then gradually sprinkled over 300 g of a spherical porous alumina carrier under dropping 90% aqueous ethanol solution in a rotary drum to coat the spherical carrier with the catalytically active components composition. Almost no lost powder was perceived during the process.
The molded product thus obtained was calcined at 310° C. for 5 hours under an air stream to obtain a coated catalyst of the present invention. The coated catalyst had an active component composition of $Mo_{10}V_{1.2}P_{1.2}Cu_{0.4}W_{0.1}$.
Then, the coated catalyst thus obtained was used for the same reaction as Example B1. Methacrolein conversion was 80.3% and selectivity to methacrylic acid was 79.1%.

Example B10

A coated catalyst of the present invention was prepared by the same procedures as in Example B9, except that 2.18 g of germanium oxide were used in place of 12-tungstophosphoric acid, 22.74 g was changed to 24.64 g in vanadium pentaoxide, 3.31 g was changed to 0 g in cupric oxide, 28.63 g was changed to 28.82 g in 85% orthophosphoric acid, and 7.54 g was changed to 11.52 g in solid cupric acetate monohydrate.
The coated catalyst thus obtained had an active component composition of $Mo_{10}V_{1.3}P_{1.2}Cu_{0.3}Ge_{0.1}$.
Then, the coated catalyst thus obtained was used for the same reaction as Example B1, methacrolein conversion was 81.9% and selectivity to methacrylic acid was 83.1%.

Example B11

In 1900 ml of pure water, 300 g of molybdenum trioxide, 24.64 g of vanadium pentaoxide, 40.83 g of 85% orthophosphoric acid, 6.78 of ceric oxide and 6.08 g of antimony trioxide were dispersed or dissolved and then stirred to heat under reflux at 95–100° C. for about 6 hours, and then added 12.18 g of cesium nitrate and further refluxed for 3 hours under heating to obtain a navy blue transparent solution.
The solution was dried by a spray drier to obtain granules and the granules were ground in a mortar into 24 mesh or less to get a powder.
The catalyst powder 310 g was mixed uniformly with 20.81 g of solid cupric acetate monohyrate corresponding to Cu 0.6 relative to Mo 10 in atomic ratio and 44.7 g of ceramic fiber to get a mixed powder. The mixed powder was then gradually sprinkled over 300 g of a spherical porous alumina carrier under dropping 90% aqueous ethanol solution in a rotary drum to coat the spherical carrier with the catalytically active components composition. Almost no lost powder was perceived during the process.
The molded product thus obtained was calcined at 310° C. for 5 hours under an air stream to obtain a coated catalyst of the present invention. The coated catalyst had an active component composition of $Mo_{10}V_{1.3}P_{1.7}Cu_{0.6}Ce_{0.2}Sb_{0.2}Cs_{0.3}$.
Then, the coated catalyst thus obtained was used for the same reaction as Example B1. Methacrolein conversion was 83.8% and selectivity to methacrylic acid was 80.2%.

Industrial Applicability

A catalyst of the present invention is industrially valuable, because it can produce methacrylic acid in a high yield and a high selectivity, and can be used for reaction under high loading condition.

What is claimed is:

1. A catalyst for producing methacrylic acid by the vapor-phase catalytic oxidation of methacrolein, comprising the active components which has a constitution represented by Formula (1) as represented below, $$Mo_{10}V_aCu_cAs_dX_eY_fO_o \qquad (1)$$

(in the formula Mo, V, P, Cu, As and O represent molybdenum, vanadium, phosphorus, copper, arsenic and oxygen respectively; X represents at least one element selected from the group consisting of Ag, Mg, Zn, Al, B, Ge, Sn, Pb, Ti, Zr, Sb, Cr, Re, Bi, W, Fe, Co, Ni, Ce and Th; Y represents at least one element selected from the group consisting of K, Rb and Cs; a, b, c, d, e, f and g represent atomic ratios of the respective elements, with $0.1 \leq a \leq 6$, $0.5 \leq b \leq 6$, $0 < c \leq 3$, $0 \leq d \leq 3$, $0 \leq e \leq 3$, $0 \leq f \leq 1$; g is the ratio determined by the valence and ratio of the other elements than oxygen), wherein copper acetate is used for all or a part of the necessary amount of a material for said Cu.

2. A catalyst according to claim 1, wherein all or a part of said copper acetate is a solid copper acetate to mix and not an aqueous solution.

3. A catalyst according to claim 2, wherein said catalyst is a mixture of solid copper acetate with a dried product of slurry containing said active components.

4. A method for manufacturing a coated catalyst for producing methacrylic acid by the vapor-phase catalytic oxidation of methacrolein, comprising:
(a) a process for mixing copper acetate and compounds containing one or more active components with water to prepare their aqueous solution or their water-based dispersion (hereinafter referred to as the slurry, including the solution and the dispersion);
(b) a process for drying the slurry prepared in the process (a) to obtain a dried slurry;
(c) a process for coating the dried slurry obtained in the process (b) on a carrier with a binder to obtain a coated product; and
(d) a process for calcining the coated product obtained in the process (c),
wherein said binder is at least one selected from the group consisting of water and an organic compound whose boiling point is 150° C. or lower at 1 atm,
and said active components have a constitution represented by Formula (1) as represented below, $$Mo_{10}V_aCu_cAs_dX_eY_fO_o \qquad (1)$$

(in the formula Mo, V, P, Cu, As and O represent molybdenum, vanadium, phosphorus, copper, arsenic and oxygen respectively; X represents at least one element selected from the group consisting of Ag, Mg, Zn, Al, B, Ge, Sn, Pb, Ti, Zr, Sb, Cr, Re, Bi, W, Fe, Co, Ni, Ce and Th; Y represents at least one element selected from the group consisting of K, Rb and Cs; a, b, c, d, e, f and g represent atomic ratios of the respective elements, with $0.1 \leq a \leq 6$, $0.5 \leq b \leq 6$, $0 < c \leq 3$, $0 \leq d \leq 3$, $0 \leq e \leq 3$, $0 \leq f \leq 1$; g is the ratio determined by the valence and ratio of the other elements than oxygen).

5. A method for manufacturing a coated catalyst for producing methacrylic acid by the vapor-phase catalytic oxidation of methacrolein, comprising:
(a) a process for mixing compounds containing each one or more active components with water to prepare their aqueous solution or their water-based dispersion (hereinafter referred to as the slurry, including the solution and the dispersion);
(b) a process for drying the slurry prepared in the process (a) to obtain a dried slurry;
(b') a process for mixing solid copper acetate with the dried slurry obtained in the process (b) to prepare a mixture;
(c) a process for coating the mixture prepared in the process (b') on a carrier with a binder to obtain a coated product; and
(d) a process for calcining the coated product obtained in the process (c), wherein said binder is at least one selected from the group consisting of water and an organic compound whose boiling point is 150° C. or lower at 1 atm,
and said active components have a constitution represented by Formula (1) as represented below, $$Mo_{10}V_aCu_cAs_dX_eY_fO_o \qquad (1)$$

(in the formula Mo, V, P, Cu, As and O represent molybdenum, vanadium, phosphorus, copper, arsenic and oxygen respectively; X represents at least one element selected from the group consisting of Ag, Mg, Zn, Al, B, Ge, Sn, Pb, Ti, Zr, Sb, Cr, Re, Bi, W, Fe, Co, Ni, Ce and Th; Y represents at least one element selected from the group consisting of K, Rb and Cs; a, b, c, d, e, f and g represent atomic ratios of the respective elements, with $0.1 \leq a \leq 6$, $0.5 \leq b \leq 6$, $0 < c \leq 3$, $0 \leq d \leq 3$, $0 \leq e \leq 3$, $0 \leq f \leq 1$; g is the ratio determined by the valence and ratio of the other elements than oxygen).

6. A method for manufacturing a coated catalyst according to claim 4 or 5, wherein a compound containing As is used to prepare the slurry in the process (a).

7. A method for manufacturing a coating catalyst according to claim 4 or 5, wherein copper oxide is used to prepare the slurry in the process (a).

8. A method for manufacturing a coated catalyst according to claim 4 or 5, wherein a compound containing As and copper oxide is used to prepare the slurry in the process (a).

9. A method for manufacturing a coated catalyst according to claim 4 or 5, wherein said binder is ethanol.

10. A method for manufacturing a coated catalyst according to claim 9, wherein said binder is a mixture having an ethanol/water ratio of 10/0–5/5.

11. A coated catalyst obtained by a method according to any of claim 4 or 5.

* * * * *

UNITED STATES PATENT AND TRADEMARK OFFICE
CERTIFICATE OF CORRECTION

PATENT NO. : 6,812,188 B2  
DATED : November 2, 2004  
INVENTOR(S) : Yoshimasa Seo et al.

Page 1 of 1

It is certified that error appears in the above-identified patent and that said Letters Patent is hereby corrected as shown below:

Column 15,  
Line 64, "$Mo_{10}V_8Cu_cAs_dX_eY_fO_g$" should read -- $Mo_{10}V_aP_bCu_cAs_dX_eY_fO_g$ --.

Column 16,  
Line 36, "$Mo_{10}V_8Cu_cAs_dX_eY_fO_g$" should read -- $Mo_{10}V_aP_bCu_cAs_dX_eY_fO_g$ --.

Column 17,  
Line 7, "$Mo_{10}V_8Cu_cAs_dX_eY_fO_g$" should read -- $Mo_{10}V_aP_bCu_cAs_dX_eY_fO_g$ --.

Signed and Sealed this

Twenty-first Day of March, 2006

JON W. DUDAS  
*Director of the United States Patent and Trademark Office*